United States Patent
Fiore

(10) Patent No.: US 6,217,569 B1
(45) Date of Patent: Apr. 17, 2001

(54) INTEGRAL SHROUD-COLLECTOR FOR URINARY CATHETER

(76) Inventor: John M. Fiore, 53 Moonlawn Rd., Troy, NY (US) 12180

(*) Notice: Subject to any disclaimer, the term of this patent is extended or adjusted under 35 U.S.C. 154(b) by 0 days.

(21) Appl. No.: 09/307,831

(22) Filed: May 10, 1999

(51) Int. Cl.[7] .................................................. A61M 27/00
(52) U.S. Cl. .......................... 604/544; 604/171; 604/271; 604/544
(58) Field of Search ...................................... 604/519, 121, 604/172, 174, 192, 198, 264, 271, 346, 347, 349, 544, 317; 206/363, 364, 438, 571

(56) References Cited

U.S. PATENT DOCUMENTS

| 3,421,509 | 1/1969 | Fiore . |
|---|---|---|
| 3,672,372 | * 6/1972 | Heimlich . |
| 3,881,199 | * 5/1975 | Treace . |
| 3,894,540 | * 7/1975 | Bonner, Jr. . |
| 4,043,345 | 8/1977 | Kramann et al. . |
| 4,062,363 | * 12/1977 | Bonner, Jr. . |
| 4,170,996 | * 10/1979 | Wu . |
| 4,652,259 | 3/1987 | O'Neil . |
| 4,957,485 | 9/1990 | Andersson et al. . |
| 5,531,717 | 7/1996 | Roberto et al. . |
| 5,792,114 | 8/1998 | Fiore . |

* cited by examiner

Primary Examiner—Anhtuan T. Nguyen
Assistant Examiner—Michael M Thompson
(74) Attorney, Agent, or Firm—Fredric Morellex

(57) ABSTRACT

A flexible, tubular envelope, termed a "shroud", for sheathing a catheter. The shroud, passing over the entire catheter, is partially disposable in the distal end of the catheter and is extractable therefrom by manipulation of the user. The shroud terminates in a closed end that includes an integral collector, a pouch/container, which has no specific definition. Devices are integrated into the shroud to aid in its manipulation, as well as in the later separation and sealing of the collector.

17 Claims, 5 Drawing Sheets

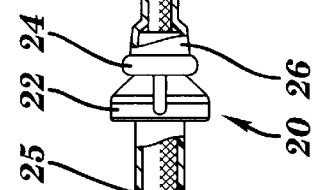
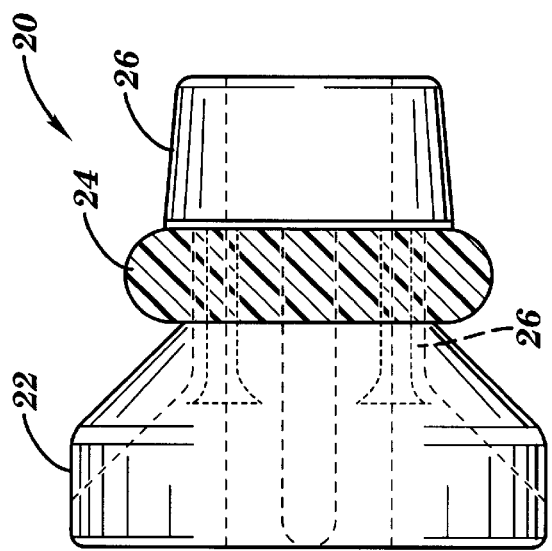

INTEGRAL SHROUD-COLLECTOR FOR URINARY CATHETER

CROSS-REFERENCES TO RELATED APPLICATIONS

U.S. patent application Ser. No. 09/169, 617, filed Oct. 9, 1998 by John M. Fiore and entitled IMPROVED CATHETER AND INTRODUCER COMBINATION, is pending and provides a priority basis for this application.

STATEMENT REGARDING FEDERALLY SPONSORED RESEARCH OR DEVELOPMENT

Not Applicable

BACKGROUND OF THE INVENTION

1. Field of the Invention

This invention relates generally to devices that are used in connection with catheters and, specifically, to membranous shrouds or envelopes that are employed to cloak a catheter in order to facilitate sterile (aseptic) insertion of such into a bodily passage. The shroud, or envelope, of the present invention eclipses the extant art by combining with it an integral, yet detachable, container element.

2. Discussion of Relevant Art

There exists in the field a need for an apparatus that will allow a medical professional to aseptically catheterize and withdraw a clean urine specimen from a patient, or allow one limited physically, say by paraplegia, to perform self catheterization and void the bladder, either fully or partially (e.g., taking a specimen sample). Although art exists that will allow aseptic or sterile catheterization and uncontaminated fluid collection/containment serially, there does not exist a combination of shroud, i.e., a sterile barrier interposable between the catheter and wall of the body passage being penetrated, and the containment element, so that these activities might be accomplished simultaneously with a unitary/singular device and under sterile conditions. The absence of such a combination does not deter medical providers so much that it hinders self-collection by those having physical limitations (ibid).

A consideration of the relevant art must begin with my U.S. Pat. No. 3,421,509 ('509), for an URETHRAL CATHETER that discloses a catheter which has inserted in its distal end (i.e., with respect to the user, who manipulates the device from its proximal end) a membranous (tubular) envelope that is extractable out of the catheter, as its distal end is advanced into the urethra. To facilitate withdrawal of the envelope, I provide an annular sleeve and guard portion, much like a collar, to slide over the catheter and which is attached to a hem of the envelope. As the catheter advances (forward) into the urethra, the sleeve is urged rearward, towards the catheter's proximal end, by manipulation or by contact against the glans/urethral orifice, and the envelope is extracted. The envelope, or shroud, of this invention does not include an integral container, but is made to engage with and connect to a pouch via the rear end of the guard portion. Such an arrangement necessitates use of an introducer element, which is non-integral to the envelope or the pouch.

Another sheathed catheter is disclosed in U.S. Pat. No. 4,652,259 ('259), entitled CATHETER ASSEMBLY. This disclosure shows a catheter disposed within an outer sheath, the outer sheath composed of two co-linear tubular members. A containment feature, providing a flexible shroud, is in reality a sterile covering that encloses the juncture of the two tubular members. Thus, its function is to maintain sterile conditions within the sheath proper and is not a container, in the conventional sense. Also relevant to the instant invention is U.S. Pat. No. 5,531,717 ('717) for NON-CONTAMINATING PROBE AND METHODS OF MAKING AND USING SAME, a sheathed catheter assembly. This patent discloses an annular collar that is attached to a hem of a sheath member and is provided in order to allow the user to manipulate (the extraction of) the sheath. However, a series of drawings in the disclosure reveal that the collar is an adjunctive construct, and not integral to the sheath. My more recent patent, U.S. Pat. No. 5,792,114 ('114), for INTRODUCER FOR STERILE INSERTION OF CATHETER, also employs a non-integral collar. The envelope (termed "shroud") therein is distinctive over the envelopes or sheaths of the aforementioned patents in that it has only one open end; but, the closed end, although possessing a small cavity, cannot be said to contain an integral fluid receptor/collector. Furthermore, the integrity of this closed-end design is violated by the operational introduction of the catheter.

Incorporation by Reference

Because of their relevance to certain features of the instant invention, as well as their provision of background art and terminology, the following previously discussed U.S. patents are hereinafter incorporated by reference: U.S. Pat. No. 3,421,509, entire disclosure; U.S. Pat. No. 4,652,259, column 2 and FIGS. 1 and 6; U.S. Pat. No. 5,531,717, FIGS. 2–9, 12, 13 and columns 1 and 2; and U.S. Pat. No. 5,792,114, entire disclosure.

Definitions

Most terms are defined parenthetically herein or may be determined by context and by referring to the drawings of both prior and the instant art. A few terms and their synonyms or analogs are defined:

"aseptic" is used synonymously with "sterile";

"bulbous" means expansive and is not meant to connote a particular shape;

"collar" means an encircling or girdling element; as an element in the present invention, it serves as a manipulative device;

"distal(ly)" refers to a device's portion that is inserted into the body, i.e., most distant from a (medical) practitioner who would ordinarily use it;

"envelope" means the flexible, membranous subject of the invention, also "sheath", "shroud";

"integral with/to" means "unitary" in the formation or realization of an object; and, "lumen" refers to a thin tube or conduit.

BRIEF SUMMARY OF THE INVENTION

Having sought, for years, to improve catheter apparatus that would promote and advance the insertion of a sterile lumen into the body, I have chosen to improve on the devices for collection of fluids that are conducted out of the body, through the lumen. More importantly, in overcoming the limitations of prior art, I have provided an integral shroud-collector that can be self-employed rather easily by a paraplegic, particularly when that person must withdraw a small amount (specimen) for analysis.

The shroud-collector is employed with a relatively short catheter of a size that can be easily handled by a person during self-insertion and when only a small collection means or container is used. This is a single situational preference, however, and is not to be viewed as a limitation of the invention. Should longer catheters be desired, particularly for general clinical usage, longer shrouds and larger, suspendable containers are to be employed.

The shroud is the entire continuous membranous, tubular envelope that has an open end, which is disposable into the distal end of the enveloped catheter, and a closed end, which is distended (bulbous) and serves integrally as a pouch/container, called a collector. An integral collar or (simply) relieved exterior surface is provided to the shroud, positioned about the distal end of the catheter, and is used to extract the shroud from the catheter during the latter's insertion, pursuant to the teachings and techniques of my previous patents (ibid) and current application. Between the collar or relieved surface and the pouch/container, an integrally formed separation mechanism, such as a tear strip or rip band is formed so that the collector may be readily separated from the shroud proper. To aid collection, particularly in cases of self-service, there is incorporated a self-sealing means, a cement or mechanical closure, in the neck portion of the collector, between the latter and the separation mechanism.

BRIEF DESCRIPTION OF THE SEVERAL VIEWS OF THE DRAWINGS

Of the Drawings:

FIG. 2 (PRIOR ART) is an illustration of a collar device;

FIG. 3 (PRIOR ART) illustrates the FIG. 2 device adapted to its envelope and installed on a catheter;

DETAILED DESCRIPTION OF THE INVENTION

Figure 1:
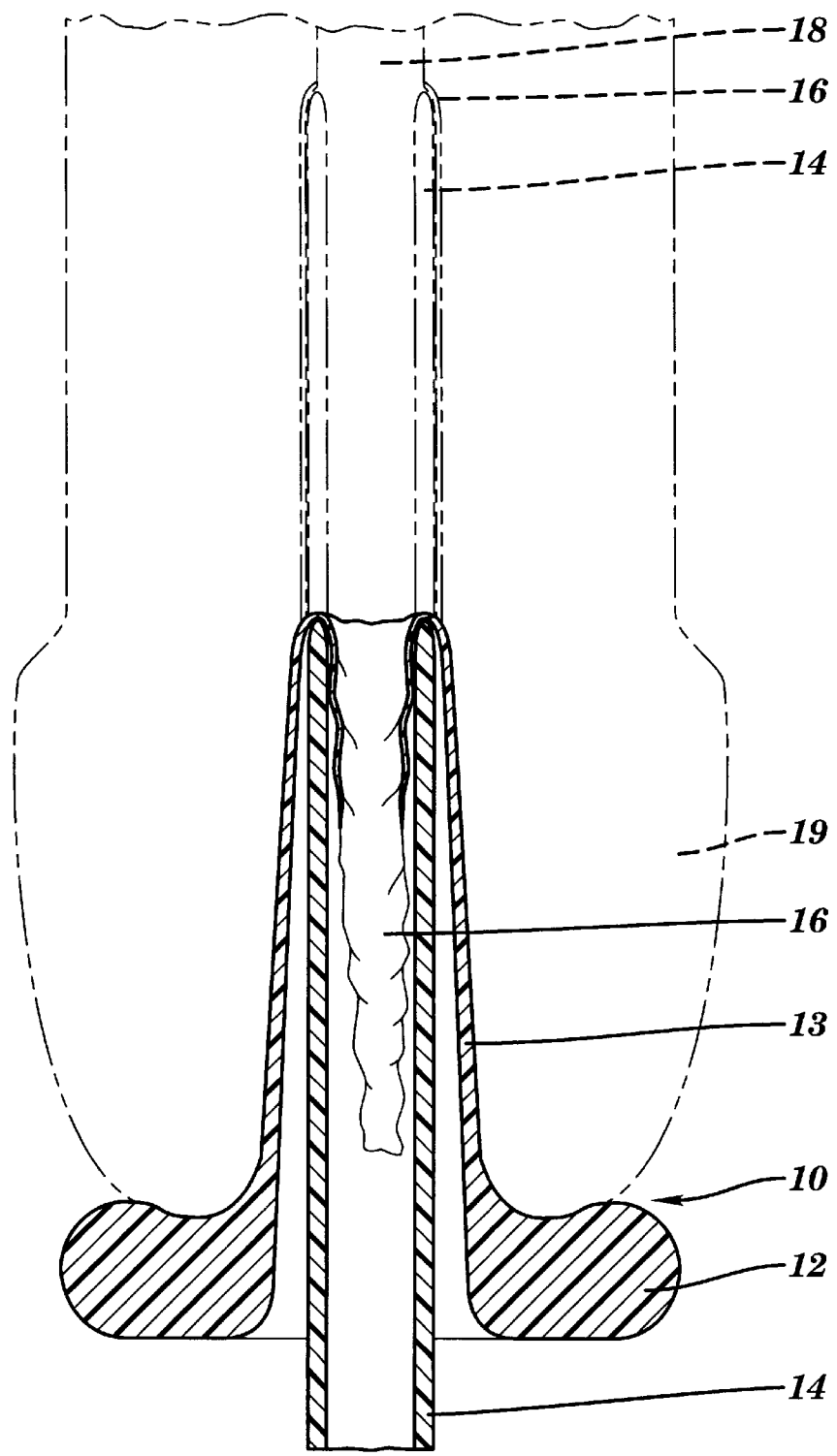
FIG. 1 (PRIOR ART) is an illustration of my first urethral catheter apparatus disclosing an extractable envelope.

Reference being had to the drawings, it will be noted that the first three are related to earlier art, FIG. 1 to my '509 (ibid) and FIGS. 2 and 3 to '717 (ibid). FIG. 1 is a disclosure of the catheter-enclosed shroud assembly 10 that I first proposed in 1969. A stop 12, or collar, is connected non-integrally to the hem of the shroud 16 via an extension 13 and fitted over the distal end of the catheter 14. In its pre-operational state (sectional, solid), the shroud is disposed into the distal end of the catheter. Once installed (phantom), the catheter has passed into the urethra 18; while, advancement of the stop 12, by engaging the gkms, is halted relative to the catheter 14. This action causes the stop to withdraw the shroud 16, depositing it about the catheter and between it and the wall of the urethra. It is essentially the above concept and apparatus that is employed in FIGS. 2 and 3, only the particular accidents varying.

FIG. 2 presents the collar assembly 20, from '717, consisting of a guide ring 22 which, via capture assembly 26, secures to it a rolled hem 24 of the disclosure's envelope (see FIG. 3). In FIG. 3, the collar assembly 20, bearing all the aforesaid elements, is seen girdling the catheter 21. The envelope 25 is depicted inside the catheter, generally at its distal end. The collar 20 is to be manipulated rearward (towards the proximal end of) over the catheter, by the user pulling on the guide ring 22, as the catheter is pressed into the urethra. The results, using this device, are quite similar to those using the '509 apparatus.

Figure 4:
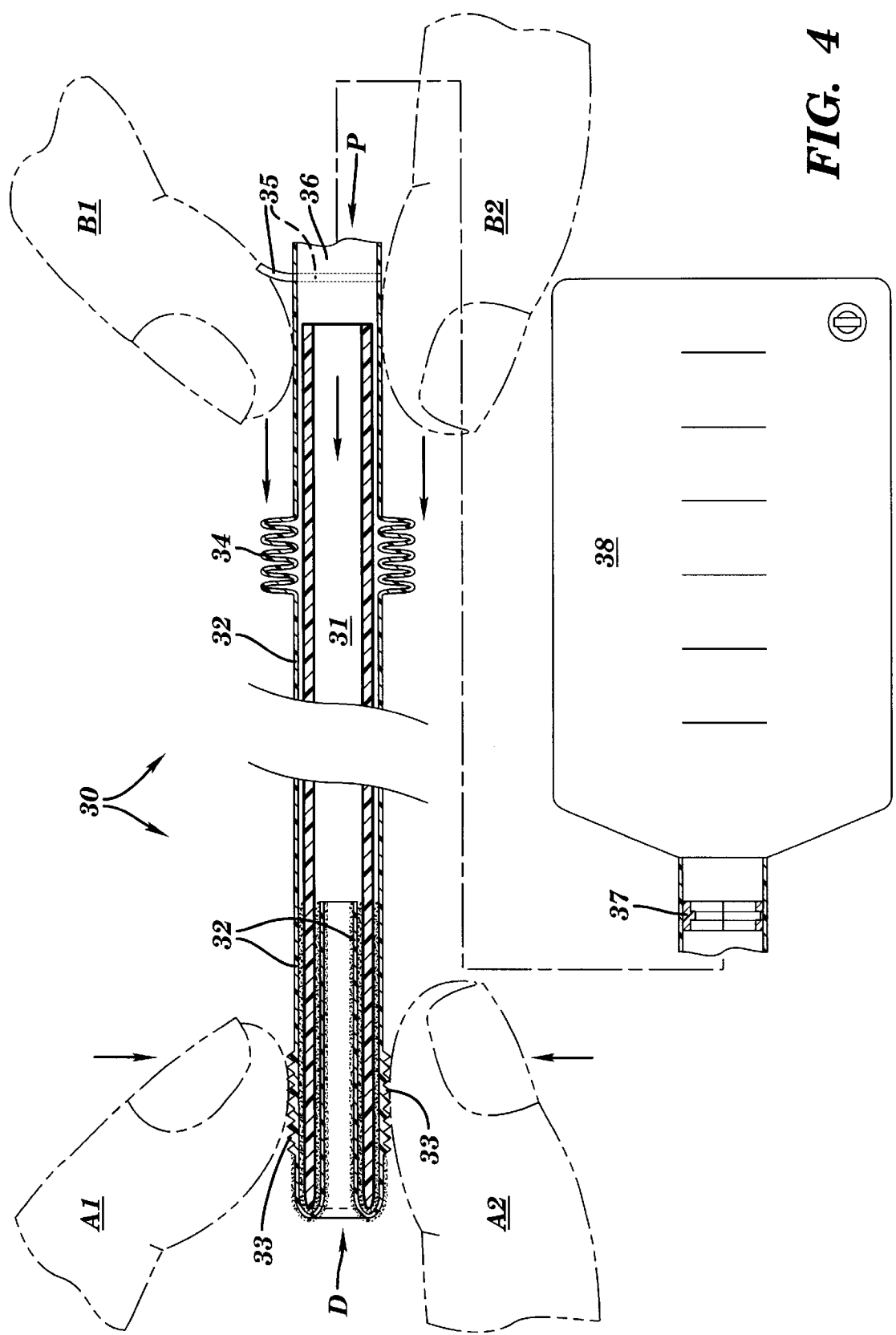
FIG. 4 is a partially sectioned drawing of the present invention.
Figure 6:
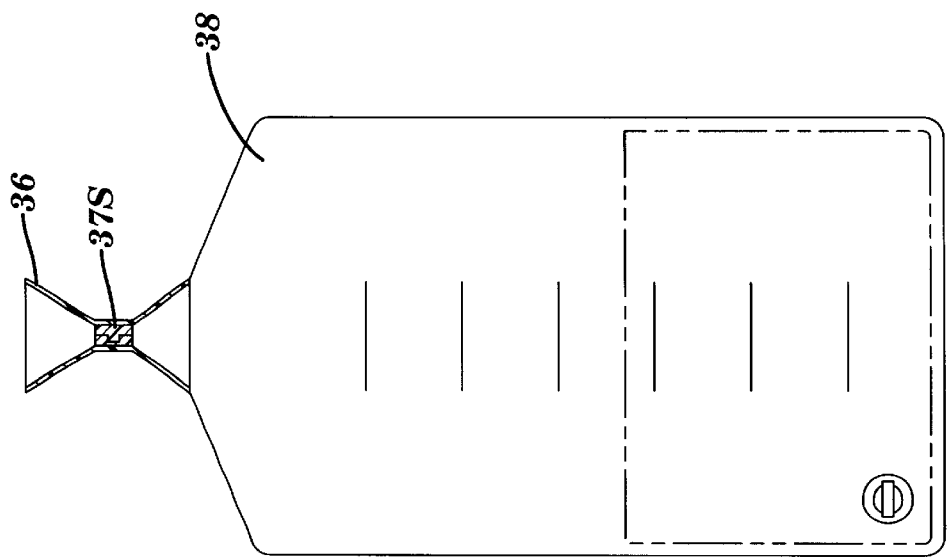
FIGS. 5 and 6 are drawings of the collector of the invention featuring separation and sealing devices.
Figure 5:
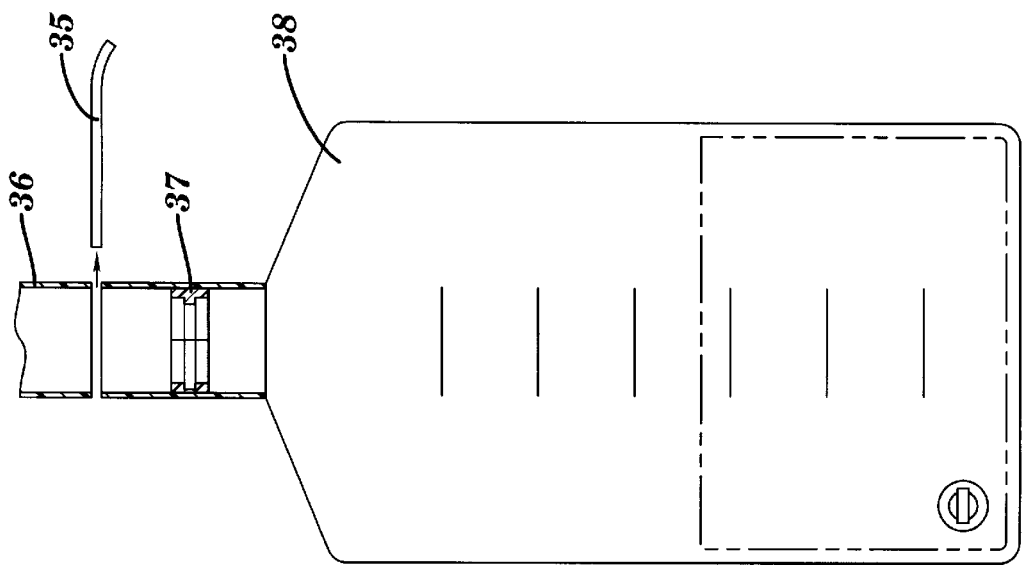

Referring now to FIG. 4, there is shown the instant invention 30, a integral shroud-collector that facilitates use by the patient who must perform self-catheterizing and, when necessary, collect a clean specimen for laboratory analysis. In order to show the salient parts of the invention, I have taken some liberty in rendering the remaining illustrations/drawings, especially in depicting sizes of the various elements of the invention in relation to each other and to human fingers, where depicted. Illustrated, but not part of the invention, catheter 31 is shown having a distal end D and a proximal end P and is a relatively short, slender, tubular device adapted for insertion into the urethra. The shroud 32 is disposed over the entire catheter, in fact, enveloping it. A surface relief 33 on the distal, exterior part of the shroud is provided as a means for digital manipulation, which is imputed by the presence of thumb A2 and finger A1. It is to be understood that the digit placement is not shown positioned correctly. The shroud is shown gathered 34 along the catheter 31. Although not necessary, this attribute may be used in the case of small specimen collection, wherein practically the entire assembly is disposed on and in the catheter. The shroud extension 36 provides adequate length to the shroud in order to incorporate integrally a separation means, i.e., a tear strip/band 35, by which the integral collector 38 becomes separable from the invention proper. The collector is an unitary containment feature that is realized by merely distending or stretching the proximal, closed end of the shroud into a bulbous, ballooned or flask shape. Techniques for accomplishing this are well known in the art. If the catheter were to be inserted into and by oneself, A1 and A2 can represent middle finger and thumb; and, the catheter may be advanced using the index finger (not shown) placed over the proximal end of the catheter. Digits B1 and B2 represent the approximate positioning of another's hand when inserting the catheter; however, in such a case, I prefer the use of a collar device in lieu of the relieved surface 33 (see FIG. 7). Final to this figure, I have provided a closure/sealing means in the neck of the collector, here a tongue-and-groove device 37, which is used to stop fluid collection (short of withdrawing the catheter) and cleanly seal the contents of the collector. Once collection and containment are achieved, the collector 38 is separated by use of tear strip/band 35. FIGS. 5 and 6 show the aforesaid process, but out of sequence, for ease of illustration. It is seen in FIG. 5 that tear strip/band 35 renders the collector 38 separable from the shroud extension 36. The tongue-and-groove mechanism 37 is shown open and, in FIG. 6, closed 37S. Alternate embodiments of this and the manipulation means are shown in the next figure.

Figure 7:
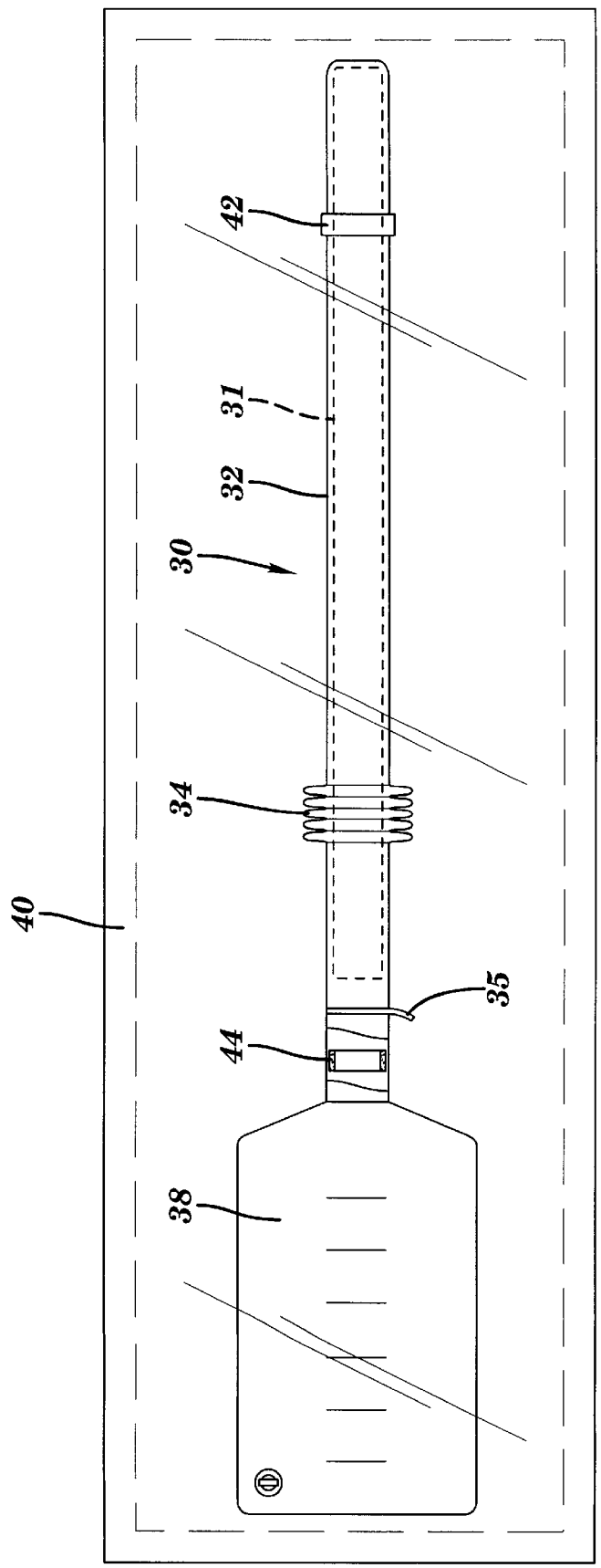
FIG. 7 is an illustration of a transparent packaging that contains the invention featuring alternate sealing and collar elements.

As depicted in FIG. 7, the packaging 40 of this invention, like that of most such appliances, poses no unforeseen difficulties. Herein, the invention 30 is assembled in sterile containment, with the catheter 31. The shroud gather 34 can be increased so as to bring the collector 38 onto the catheter, resulting in a more compact package. Noteworthy in this figure are alternate embodiments, closure 44 and integral collar 42. These are, respectively, an inner deposit of a cement, such as a wettable adhesive or a selective cohesive that is activated by wetting or by finger pressure exerted on the outer surface of the shroud over the closure 44, and an integrally formed collar that acts as a stop in much the same manner as that part did in my '509 patent, but is also adapted to function as a finger purchase to aid in manipulation. As a stop, the collar 42 is intended to abut the opening to the urethra in either female or male patients. It may be a greatly thickened part of the shroud or a resilient annulus that is molded into it. Both of these alternate embodiments, as well a their variations, are realizable with the current state of the art.

Having set forth my invention in the preferred embodiment, and in what I feel to be the best mode at this time for accomplishing both imputed and implied purposes, I here now commend its use to the field, consistent with the spirit of the disclosure and constrained by the appended claims.

What is claimed is:

1. In a flexible tubular envelope for sheathing a catheter, the catheter having a distal open end adapted for insertion into a urethra and a proximal open end from which body fluids exit, the envelope having a collar formed between a first open end and a second open end thereof, said first open end being disposable within and extractable from out said distal end of the catheter by movement of the collar towards said proximal end, an improvement comprising:

said envelope including a continuously formed fluid conduit and a bulbous container that comprises an integrally made, unitary extension of said second end of the envelope, said container adapted to receive therein said body fluids;

a manipulation means formed integrally into the envelope and disposed between said first and said extension; and a separation strip for rending the envelope, said strip disposed between said manipulation means and said container, whereby the container is made separable from the envelope.

2. The improvement of claim 1 further comprising a closure means disposed on an interior wall of the envelope between said strip and said container whereby, upon separation of the container, it becomes sealable.

3. The improvement of claim 2 wherein said closure means comprises a sealer band.

4. The improvement of claim 3 wherein said sealer band comprises a cement.

5. The improvement of claim 3 wherein said sealer band comprises a tongue-and-groove joint means.

6. The improvement of claim 1 wherein said manipulation means comprises an externally relieved surface on the envelope that facilitates grasping by a user's thumb and finger.

7. An improved shroud having duality of purpose by providing both aseptic envelopment of a catheter and containment of a fluid specimen taken therewith comprising:

a tubular membrane having a first open end and a closed second end, said second end defined by a bulbous reservoir;

an integral manipulation means disposed about the membrane between said first end and said second end; and a rendable band disposed about the membrane between the manipulation means and said second end.

8. The shroud of claim 7 wherein said manipulation means comprises an externally relieved surface on the envelope that facilitates grasping by a user's thumb and finger.

9. The shroud of claim 7 further comprising a closure means circumscribing the membrane and disposed interior thereof between said band and said second end.

10. The shroud of claim 9 wherein said closure means comprises a cement.

11. The shroud of claim 9 wherein said closure means comprises a tongue-and-groove joint means.

12. An integral, unitary and continuously made shroud-collector device for aseptically using an urethral catheter and for collecting, conducting and containing a fluid specimen flowing out of the catheter, the device comprising a tubular shroud membrane having a first open end, a second closed end and adapted for enveloping the catheter, said first open end insertable into and withdrawable from out a distal end of the catheter, said shroud membrane bearing a manipulation means disposed between said first open end and said second closed end, said second closed end further defined by an unitary and integrally made and mechanically separable bulbous extension of the shroud membrane which comprises the collector of said device.

13. The device of claim 12 further comprising a rendable band disposed about the shroud membrane between the manipulation means and said second closed end.

14. The shroud of claim 13 wherein said manipulation means comprises an externally relieved surface on the envelope that facilitates gasping by a user's thumb and finger.

15. The shroud of claim 14 further comprising a closure means circumscribing the membrane and disposed interior thereof between said band and said second end.

16. The shroud of claim 15 wherein said closure means comprises a cementing material.

17. The shroud of claim 16 wherein said closure means comprises a tongue-and-groove joint means.

* * * * *